United States Patent [19]

Singer

[11] Patent Number: 5,492,471
[45] Date of Patent: Feb. 20, 1996

[54] HEALING CAP SYSTEM

[75] Inventor: Gary Singer, 245 S. Pennell Rd., Middletown Media, Pa. 19063

[73] Assignees: Gary Singer, Media; Phillip Singer, Upper Darby; Michael Ginn, Merion Station; Neil Gottehrer, Havertown, all of Pa.

[21] Appl. No.: 216,908

[22] Filed: Mar. 23, 1994

[51] Int. Cl.[6] .................... A61C 13/12; A61C 13/225; A61C 8/00
[52] U.S. Cl. ............................................. 433/172; 433/173
[58] Field of Search ................................. 433/172, 173, 433/174, 175, 176

[56] References Cited

U.S. PATENT DOCUMENTS

| | | |
|---|---|---|
| 5,035,619 | 7/1991 | Daftary. |
| 5,073,111 | 12/1991 | Daftary. |
| 5,145,372 | 9/1992 | Daftary et al.. |
| 5,246,370 | 9/1993 | Coatoam. |
| 5,297,963 | 3/1994 | Daftary .............................. 433/173 X |
| 5,316,476 | 5/1994 | Krauser .................................. 433/173 |
| 5,336,090 | 8/1994 | Wilson, Jr. et al. ................ 433/173 X |
| 5,368,483 | 11/1994 | Sutter et al. ............................ 433/173 |

Primary Examiner—Nicholas D. Lucchesi
Attorney, Agent, or Firm—Caesar, Rivise, Bernstein, Cohen & Pokotilow, Ltd.

[57] ABSTRACT

An anatomically dimensioned healing cap is provided for use during second stage surgery of a dental implant which preserves the actual tooth contour within the gingiva to facilitate accurate crown reproduction exhibiting a proper emergence profile. The healing cap has a housing that is dimensioned in accordance with the removed tooth and has a releasably securable insert that directly engages the head of any implant without scoring or damaging the implant. For posterior teeth, the healing cap can preserve the tooth cavity in the gingiva tissue even if the implant is mounted off-center of the original tooth location. The healing cap also provides an occlusal lip to prevent the overgrowth of gingiva tissue during second stage healing. Plastic burnout sleeves and cylinders are provided to enable dental technicians to more accurately and more efficiently create a crown or bridge. Healing cap models and an implant alignment indicator are provided to enable the dental surgeon to more accurately locate and align a dental implant in the initial stages of surgery.

23 Claims, 9 Drawing Sheets

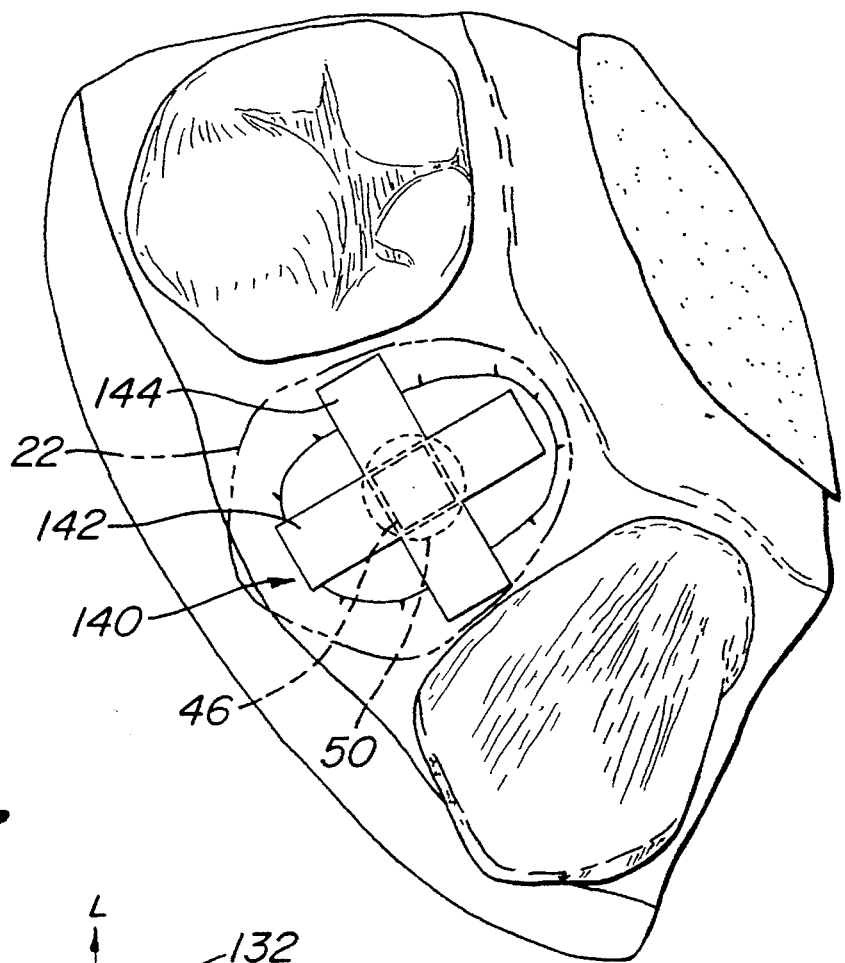
FIG. 6
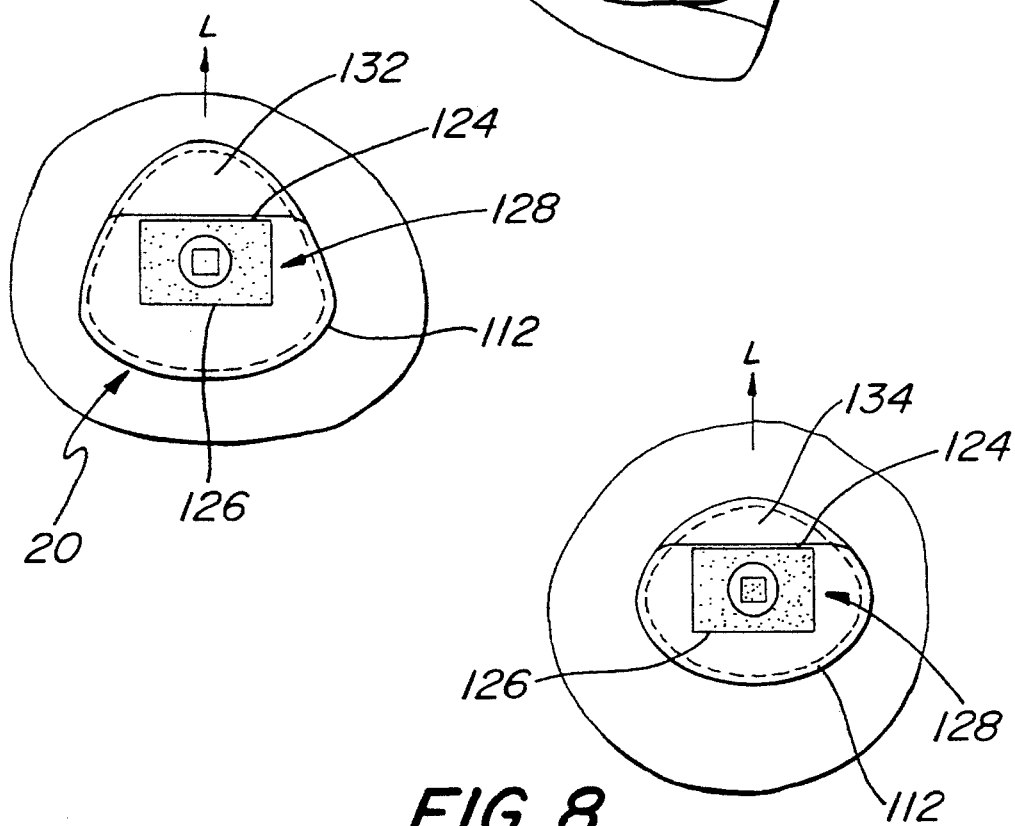
FIG. 7
FIG. 8

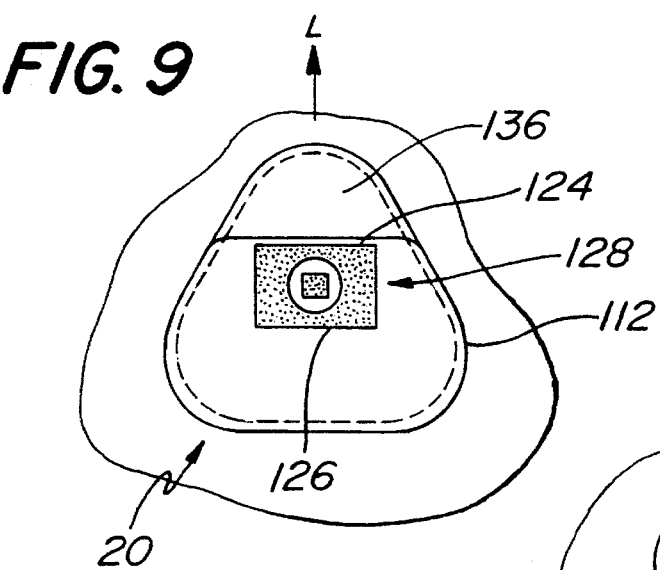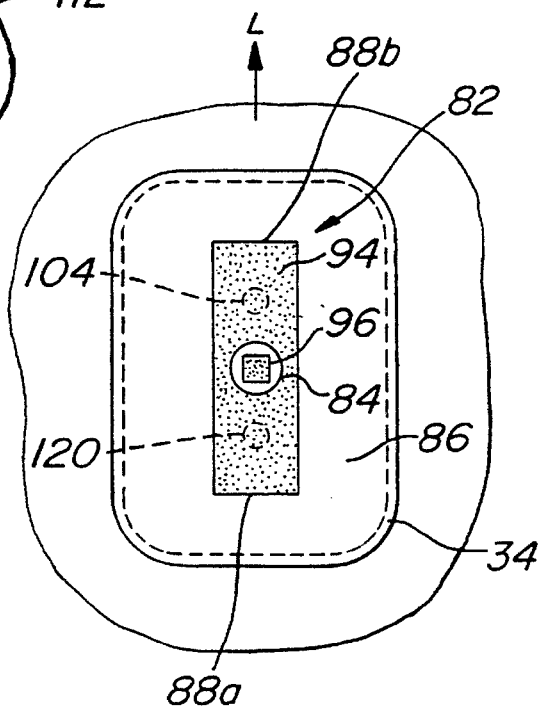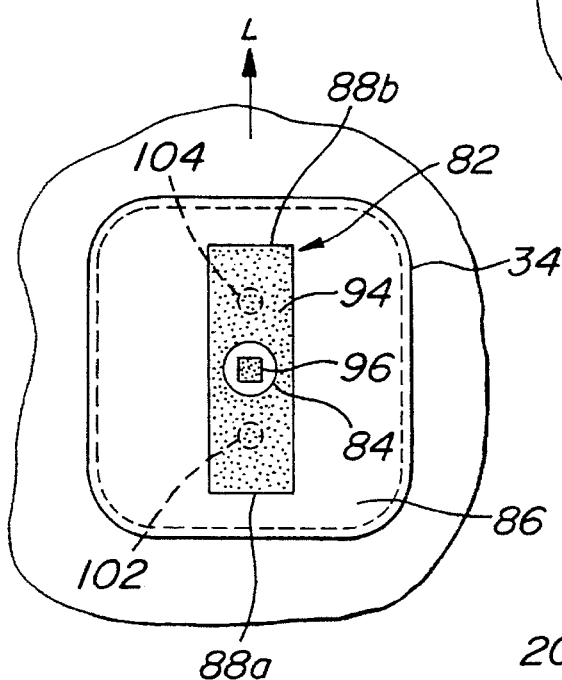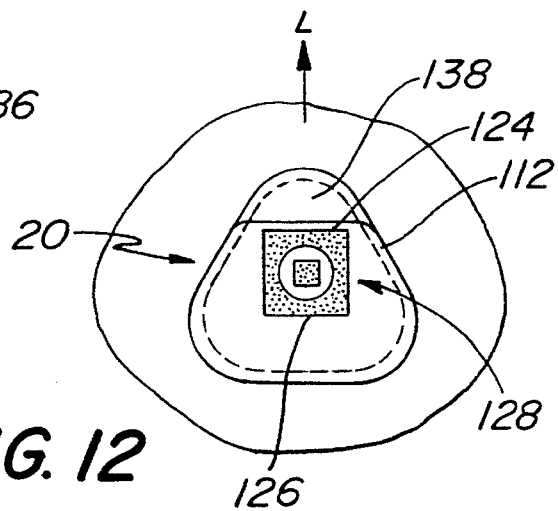

5,492,471

HEALING CAP SYSTEM

FIELD OF THE INVENTION

This invention relates generally to the field of dental implants, more particularly, to apparatus of second stage healing caps for correctly aligning dental implants into the patient's bone and providing accurate crown or bridge insertion into the gingiva.

BACKGROUND OF THE INVENTION

Having a crown or bridge affixed to a patient is achieved by basically a three stage process.

In the first stage, the dental surgeon removes the dead or cracked natural tooth. The surgeon then cuts down through the gingiva (i.e., the gum which held the tooth) to expose the underlying bone. The surgeon then burrs into the bone to insert a dental implant. The dental implant will act as the permanent anchor for the crown (which will be created during the third stage). The implant basically comprises a threaded bore to receive a retaining screw that is coupled at some portion to the crown. The crown is then secured to the dental implant by that retaining screw. The dental implant itself can be either press-fitted down into a hole drilled in the bone or it can be screwed down into that hole. The dental implant may have a male or female anti-rotational coupling (e.g., an external hex or internal hex, respectively) but in any case the entrance to the screw hole is located in the center of the anti-rotational coupling. A cover is then placed over the screw hole in the center of the anti-rotational coupling and the overlying gingiva tissue is then closed back over the implant. It is extremely important that sufficient time be allotted for osseointegration, i.e., the surrounding bone secures itself around the dental implant. This is achieved by allowing 3–4 months of healing time for dental implants in the lower jaw and 5–6 months of healing time for dental implants in the upper jaw.

Following this first stage healing, second stage healing begins. In particular, the surgeon cuts away the gingiva surrounding the head of the dental implant, removes the cover and then inserts a second stage healing cap which is releasably secured (e.g., screwed down) onto the head of the dental implant. A typical second stage healing cap is either cylindrical in form and/or circular in cross-section. In all cases, the healing cap is designed to maintain a cylindrical chamber, during second stage healing, from the gingiva crest (the top of the gum) down to the opening in the dental implant.

After approximately three weeks, the stitches are removed and the restorative doctor and dental technician then begin the third stage: creating a crown that is permanently secured to the dental implant. In particular, the healing cap is removed and a transfer impression is taken of the jaw containing the implant. The transfer impression basically is a mold that transfers the patient's dental information from the patient to a stone model. To preserve the location of the opening to the dental implant when creating the stone model, an impression post is coupled to the head of the implant. The impression post transfers the position information of the dental implant in the patient's mouth to the stone model. The impression post also prevents the transfer impression mold from entering into the opening to the dental implant.

When the transfer impression is completed and removed from the patient's mouth, the impression post is disengaged from the dental implant and reinserted into the hole preserved in the transfer impression. An implant analog is then attached to the impression post and the stone model is ready to be made.

The healing cap is then reinserted into the dental implant in the patient's mouth to continue to preserve the cavity in the gingiva until either the temporary and, eventually, the permanent crown is in place. A stone model is created from the transfer impression and the stone model becomes the model from which the restorative doctor and the dental technician create the crown/bridge. It is the model of the cavity, preserved in the stone model, that determines the final shape of the crown/bridge.

The following constitute various examples of United States patents disclosing healing cap systems.

For example, U.S. Pat. No. 5,073,111 (Daftary) discloses a healing cap system in the form of a custom dental implant that is embedded in the jawbone and which can receive frusto-conical shaped healing caps and any one of three abutments that have different emergence profiles. Although this patent states that the healing caps are dimensionally similar to the tooth previously removed, the healing caps are all circular in cross-section and do not differentiate among the various possible tooth dimensions. Furthermore, the healing cap in this patent is coupled to the implant by being rotated so that the threaded surface of the healing cap is secured within the implant bore. Although the healing cap has a custom socket that fits over a raised lip on the implant head without damaging the lip during securement, use of this same healing cap with other conventional implants may damage the antirotational coupling on these types of implants. In addition, rotation of the healing cap to secure it to the implant may damage the surrounding gingiva tissue.

In U.S. Pat. No. 5,035,619 (Daftary), which is a continuation-in-part of the 5,073,111 patent, there is disclosed a two-piece (upper and lower) healing cap similar in design to the healing caps disclosed in the U.S. Pat. No. 5,073,111. The added feature of having an upper and lower portion of a healing cap permits the lower part of the healing cap (which engages the dental implant) to remain in place while the upper part is removed and the abutment (the stem which the crown will be formed upon in the third stage) is then coupled to the lower part of the healing cap, instead of having to attach the abutment directly to the implant. However, the deficiencies of the healing cap of the U.S. Pat. No. 5,073,111 remain in the healing caps of the U.S. Pat. No. 5,035,619.

U.S. Pat. No. 5,145,372 (Daftary) is also a continuation-in-part of the U.S. Pat. No. 5,073,111 and discloses a reinforced two-part healing cap. To that end, the lower part houses a threaded shaft rather than a threaded bore while the upper part houses a threaded bore. As in the U.S. Pat. No. 5,035,619, the upper part can be removed and an improved abutment, i.e., an abutment having a threaded bore, can be engaged to the lower part of the healing cap, instead of having to attach the abutment directly to the implant. However, as with the U.S. Pat. No. 5,035,619 healing cap, this improved two-part healing cap retains the same deficiencies of the healing caps of the U.S. Pat. No. 5,073,111.

In U.S. Pat. No. 5,246,370 (Coatoam) there are disclosed custom dental implants comprising an open upper portion which has the same general nonuniform shape of a removed tooth bone cavity. The implants have cylindrical prongs that are embedded into the patient's jawbone. The upper portion of the implant is shaped like the removed tooth and has matching inserts that fit within the upper portion. Each insert has a lower portion that is also shaped like the particular tooth removed (in order to seat within the upper portion of the implant) and a upper portion that is circular in cross section.

As an example of healing caps in the market, there is the Anatomic Abutments System™ sold by Dental Imaging Associates, Inc. of Sunrise, Florida which includes a cylindrical healing cap that is screwed down into the dental implant.

The problem with using a cylindrical healing cap is that a cylindrical cavity in the gingiva (which the typical healing cap creates during second stage surgery) does not imitate the dental anatomy of a tooth within the gingiva tissue. In other words, the actual periphery of the tooth that is in the gingiva tissue has a cross section that is not circular but rather has something similar to facets. Maintaining the facet structure within the gingiva is necessary to create a crown that has the proper emergence profile with respect to the gingiva. However, by using a cylindrical healing cap, the restorative doctor and dental technician must wax up the crown from a cylindrical opening in the gingiva (left by the cylindrical healing cap) which is not at all representative of the tooth that once resided there. It may be true that a cross section taken at one particular depth within the gingiva may happen to be circular but that is not true for the entire cross section of the tooth that resides in the gingiva.

As one skilled in the art can appreciate, the task of the restorative doctor and dental technician is difficult because the they are trying to create a crown from a somewhat flat gingiva surface, i.e., there is no natural tooth crater that guides them in molding a tooth. In addition, the crown and gingiva interface that the restorative doctor and dental technician are trying to create cannot easily replicate the tightly sealed interface that a natural tooth growing out of the gingiva would have.

Furthermore, once the dental implant is in place, the restorative doctor and dental technician have no room for adjusting the orientation of the tooth, i.e., the crown screw hole must be perfectly aligned with the vertical chamber left by the healing cap or else the crown will not be positioned correctly. Creating a crown which has a portion that must drastically taper to conform to the cylinder head of an implant is improper and thereby does permit the stimulation of soft tissue.

Moreover, where external hex implants are used (i.e., dental implants having a hexagonal-shaped anti-rotational coupling projecting upwards) the conventional cylindrical healing caps do not engage and seat over the hex but rather must be secured on top of the hex. In particular, on external hex implants the procedure to date is to select a separate spacing abutment to place over this particular type of implant that will allow the emergence procedure to begin at the gingival crest (the top surface of the gum). Because healing caps on these type of implants are also of a circular design, the height of the healing caps are frequently placed too high. The healing caps come in different millimeters of height. When the healing cap is above the height of gingival tissue the circumference of metal will show.

The result of all of this is that the restorative doctor and dental technician are trying to formulate a crown/bridge from criteria that are lost.

Therefore, a need exists for apparatus for creating and then maintaining the natural gingiva cavity throughout second stage healing that allows a restorative doctor and dental technician to easily and accurately create a close replica of the removed tooth that not only looks natural (i.e., being aligned with surrounding teeth and having proper tooth emergence profile from the gingiva) but also avoids soft tissue degeneration and destructive plaque build-up.

Furthermore, there is a need for a second stage healing cap that is compatible with a variety of standard dental implants and whereby the healing cap does not score or damage the anti-rotational coupling of the implant whenever the cap is engaged/disengaged from the implant.

OBJECTS OF THE INVENTION

Accordingly, it is the general object of this invention to provide apparatus which address the aforementioned needs.

It is a further object of this invention to provide an alignment device for checking the buccal, lingual, mesial and distal orientation of a dental implant before the implant is permanently inserted into the bone of the patient.

It is another object of this invention to provide apparatus that the surgeon can place during first stage surgery on top of the implant and fold the surrounding tissue over to ascertain whether there is enough depth of soft tissue and/or compensate for by shaving bone, if necessary.

It is still yet another object of this invention to provide a way to ascertain earlier on in dental surgery whether a graft will be needed to enhance the depth of soft tissue emergence profile.

It is yet another object of this invention to provide a healing cap that provides a dental anatomical replica of any natural tooth wherein the replica is inserted in the gingiva, at the proper tooth location, during second stage healing to maintain the proper emergence profile of the natural tooth.

It is yet a further object of this invention to provide a reusable healing cap that can be releasably secured to any dental implant without scoring or damaging the anti-rotational coupling of the dental implant.

It is still a further object of this invention to provide an anatomically designed healing cap of a posterior tooth for use during second stage healing wherein the healing cap compensates for a more lingually or more buccally located dental implant, thereby maintaining the proper arch formation of the crown with respect to surrounding teeth.

It is still another object of this invention to provide a healing cap having an occlusal lip around the top to inhibit the overgrowth of gingiva tissue during second stage healing.

It is still another object of this invention to provide a healing cap that enables a crown to be created having proper tooth contour thereby avoiding soft tissue retardation that usually occurs when crowns having improper tooth contours are used.

It is still another object of this invention to provide a healing cap that enables a crown to be created having proper tooth contour, thereby avoiding soft tissue recession which permits food impaction under the crown that usually occurs when crowns having improper tooth contours are used.

It is still another object of this invention to provide apparatus that enables a crown to be created having proper tooth contour, thereby allowing occlusion function of food to stimulate tissue at the gingival area that does not occur when crowns having improper tooth contours are used.

It is still another object of this invention to provide apparatus that enables a crown or bridge to be created having proper tooth contour thereby avoiding destructive plaque build-up between the crown and gingiva that usually occurs when crowns having improper tooth contours are used.

It is still another object of this invention to provide a method for avoiding interference between multiple adjacent implants by the use of healing cap dowels and alignment indicators during first and second stage surgery.

It is still another object of this invention to provide apparatus for maintaining sufficient embrasure room for cleaning between multiple adjacent crowns by the use of healing cap dowels and alignment indicators during first and second stage surgery.

It is still another object of this invention to provide apparatus for facilitating and increasing the accuracy of creating cementable or screw-down types of crowns for use with any restorative castable cylinder.

It is still yet another object of this invention to provide a surgery kit that provides the dental surgeon with all the necessary healing caps, alignment indicators and related apparatus for locating and verifying dental implant locations, including healing cap positioning and alignment.

It is still yet another object of this invention to provide a laboratory kit that provides the dental technician with healing cap dowels, burnout sleeves and hollow cylinders necessary for creating the crown.

SUMMARY OF THE INVENTION

These and other objects of the instant invention are achieved by providing a healing cap to be used in a predetermined position in the gingiva tissue of a patient during second stage surgery of a dental implant for mounting a crown replicating the tooth naturally residing at that position. The implant has a head with an anti-rotational coupling. The healing cap forms a cavity in the gingiva tissue whose shape replicates a portion of the tooth. The healing cap comprises a housing and an insert. The housing has an outer surface including portions having at least two predetermined dimensions which comprise the mesio-distal dimension of the neck of the tooth and the labio-lingual dimension of the neck of the tooth. These dimensions are representative of the anatomical dimensions of the corresponding portions of the tooth which was located within the gingiva tissue. The insert has a coupling means to engage the anti-rotational coupling on the head of the dental implant. This anti-rotational coupling also forms the opening to a threaded bore of the implant. The insert is releasably secured inside the housing by a securement means. The housing, the coupling means of the insert and the anti-rotational coupling of the dental implant are aligned to allow passage of a retaining screw through the housing, the insert and the dental implant in order to secure the healing cap against the head of the dental implant.

DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 6 is a plan view like that of FIG. 1 but showing an alignment device constructed in accordance with another aspect of this invention;

FIG. 7 is a top plan view of a Category I healing cap;

FIG. 8 is a top plan view of a Category II healing cap;

FIG. 9 is a top plan view of a Category III healing cap;

FIG. 10 is a top plan view of a Category V healing cap;

FIG. 11 is a top plan view of a Category VI healing cap;

FIG. 12 is a top plan view of a Category VII healing cap;

DESCRIPTION OF THE PREFERRED EMBODIMENT OF THE INVENTION

It must be stated from the outset that because many of the maxillary (upper) and the mandibular (lower) teeth have dental anatomy dimensions that are similar (see Tables A and B), there need be only seven categories (I–VII) of second stage healing caps (occlusal views depicted in FIGS. 1 and 7–12) constructed in accordance with the present invention in order to enable a crown to be made for any tooth. As will be discussed in detail below, each category of healing cap is made up of a housing and a corresponding insert. Categories I–III and VII are healing caps for use with anterior (front) teeth, whereas Categories IV–VI are healing caps for use with posterior (back) teeth. Suffice it to say for now, the healing cap used with anterior teeth is structurally different from the healing cap used with posterior teeth. Therefore, although it is unnecessary to discuss all seven categories of healing caps, it is necessary to separately discuss a healing cap category used with posterior teeth and a healing cap category used with anterior teeth.

Figure 1:
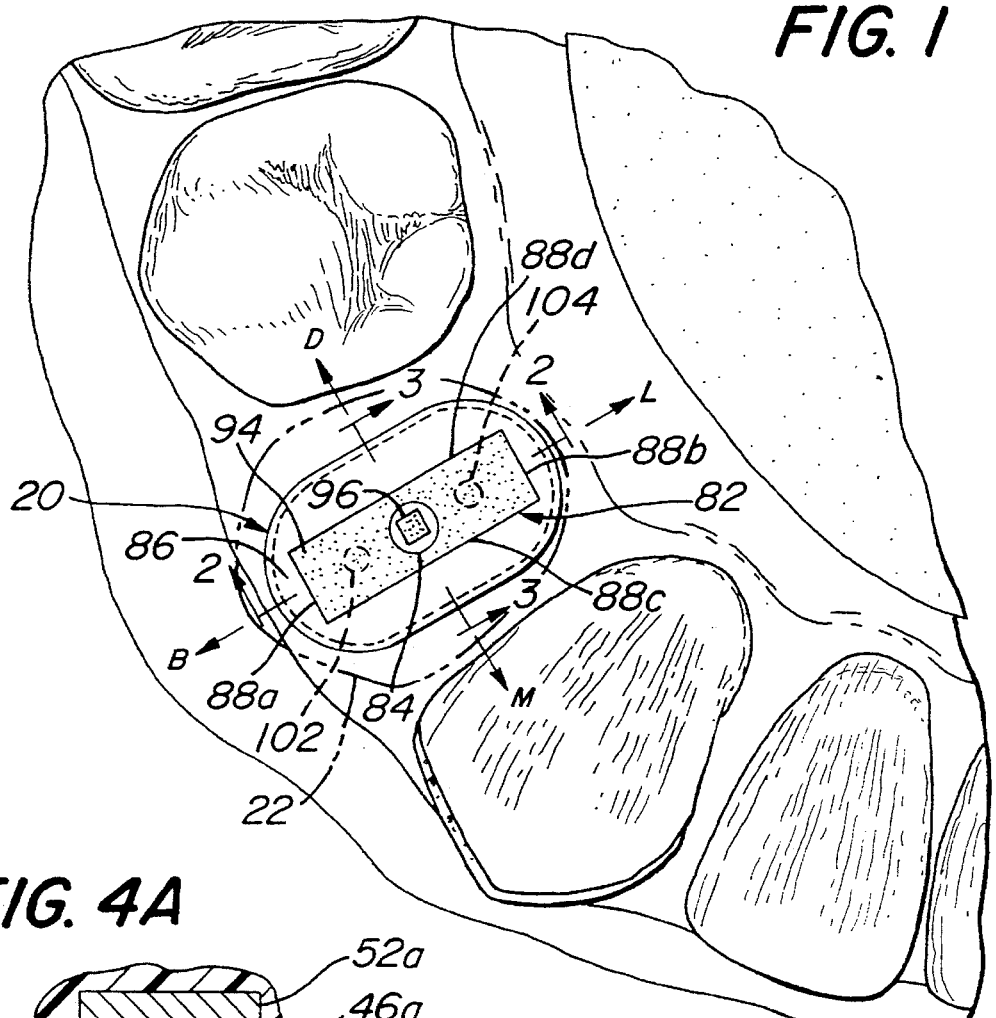
FIG. 1 is an occlusal (top) plan view of a Category IV healing cap constructed in accordance with one aspect of this invention and shown inserted in the lower jaw.

Referring now in greater detail to the various figures of the drawing wherein like reference characters refer to like parts, a "Category IV" second stage healing cap constructed in accordance with the present invention is shown generally at 20 in FIG. 1. The healing cap 20 is part of a complete system (to be described later) and is used to form a cavity or crater 32 in the gingiva tissue 28 above an implant 30 to receive a crown 170a or 170b (FIGS. 16 and 17) replicating the tooth that had naturally resided there. In the exemplary embodiment shown in FIG. 1, the healing cap 20 is inserted in the patient's lower right jaw where a mandibular first bicuspid tooth 22 once resided (shown by phantom lines). (A Category IV second stage healing cap was selected as an example of a healing cap used with a posterior tooth. Therefore, the following discussion is suitable for all other healing caps 20 that are used with posterior teeth, i.e., Categories V and VI).

Figure 2:
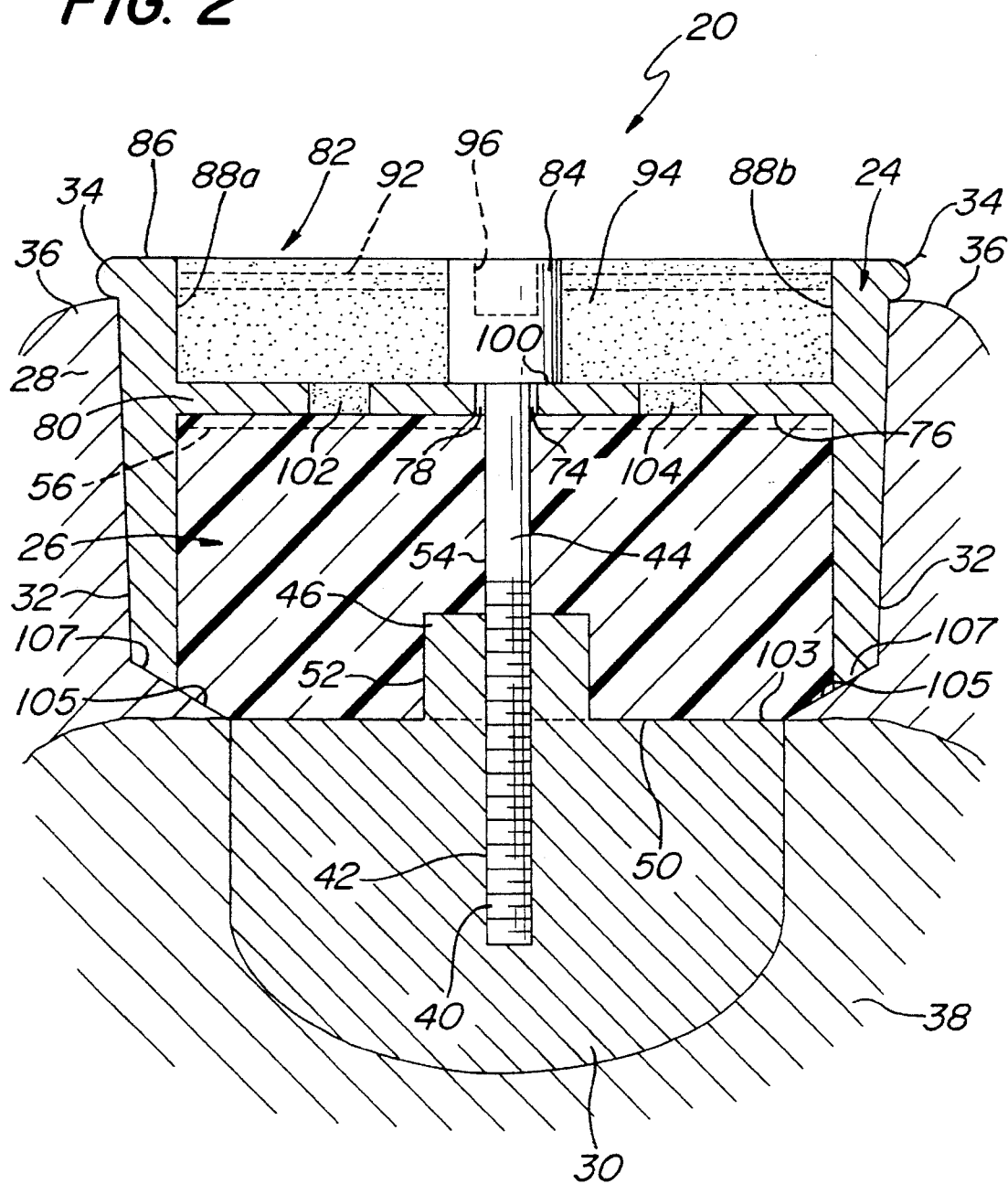
FIG. 2 is an enlarged sectional view taken along line 2—2 in FIG. 1.

As can be seen more clearly in FIG. 2, the healing cap 20 basically comprises two parts, a healing cap housing 24 and an insert 26. The housing 24 comprises a reusable titanium material, whereas the insert 26 is preferably formed of a plastic and is disposable or autoclaved for re-use. The importance of these respective materials is that titanium is resilient and compatible with gingiva tissue, whereas plastic is better suited for engaging the dental implant 30 because plastic does not mar or score the metal head of the dental implant during securement of the healing cap 20 to the implant. It should be understood that although the inserts 26 for posterior healing caps 20 have similar designs, the inserts 26 are not interchangeable with the housings 24 of another posterior healing cap 20 category, i.e., the insert 26 of a Category IV healing cap 20 can only fit within the housing 24 of a Category IV healing cap.

In accordance with one aspect of this invention, the housing 24, has the dimensions of the first bicuspid tooth 22 which had resided in the gingiva tissue 28. The housing is positioned in the gingiva tissue 28 at the desired site, i.e., where the first bicuspid tooth 22 resided, during second stage healing, thereby establishing a crater 32 in the gingiva tissue 28 that accurately resembles the recess in the gingiva tissue 28 that once surrounded the first bicuspid tooth 22.

In accordance with a preferred embodiment of this invention, each housing has predetermined crucial dimensions corresponding to at least the mesio-distal dimension and the labio-lingual dimension which describes the periphery of the tooth, from the bone upward through the gingiva. In fact, the housing may be made using in addition to the mesio-distal dimension and the labio-lingual dimensions other well known tooth dimensions such as those set forth in Tables A and B herein. These tables are based on the two tables found in *Tooth Anatomy* by Dr. Henry A. Linek, D.D.S., copyright 1948 and 1949. The two crucial dimensions are designated by an asterisk in the Tables A and B.

As can be seen clearly in FIG. 2, an occlusal lip 34 forms the top periphery of the housing 24. This lip 34 ensures that the gingival crest 36 (i.e., the top surface of the gingiva tissue) does not resorb during second stage healing, thereby preventing the gingiva tissue 28 from closing up the crater 32. Without the lip 34, the gingiva tissue 28 would grow over the top of the housing 24 during second stage healing. In particular, when the gingiva tissue 28 is cut in order to insert the healing cap 20, the incision is made in a mesial-distal orientation. After the healing cap 20 is releasably secured to the dental implant 30, the sliced gingiva tissue 28 is pressed together around the healing cap 20 and under the occlusal lip 34; stitches in the buccal-lingual direction are then made across the sliced gingiva tissue 28 wherein second stage healing begins.

The insert 26 of the healing cap 20 serves as coupling means for securing the healing cap 20 to the implant 30. In order to best understand the construction and operation of the coupling means, it is necessary to first discuss the structure of and method of use of conventional dental implants.

To that end, during first stage surgery, the dental implant 30 is permanently secured in the patient's jaw bone 38. Generally, dental implants have a central bore that receives the threaded end of a retaining screw in order to enable a conventional healing cap or crown to be secured to the implant. FIG. 2 shows a conventional dental implant 30 having a central bore 40 that receives the threaded end 42 of a retaining screw 44. The screw 42 secures the healing cap 20 to the implant 30, as will be discussed later. Conventional dental implants typically have an anti-rotational coupling, male or female, located at the top or head of the implant which engages a mating female or male coupling, respectively, of the crown to prevent the crown from rotating on top of the implant during securement. The opening to the central bore 40 is located in this mating female or male coupling. Thus, as can be seen in FIG. 2, the dental implant 30 has a male (external) anti-rotational coupling 46, having an opening 48, located on the head 50 of the implant 30.

The healing cap insert 26 of this invention has a mating female anti-rotational coupling 52 which seats around the implant coupling 46 during engagement while aligning a central insert bore 54 with the opening 48. This alignment permits the passage of the threaded end 42 of the retaining screw 44 through the healing cap 20 and down into the implant 30. It is important to understand that the insert 26 of the present invention can be manufactured to have a male anti-rotational coupling to engage a dental implant which has a female anti-rotational coupling located at its head 50. The depiction of a female anti-rotational coupling 52 in the insert 26 is by way of example, not limitation.

Figure 4A:
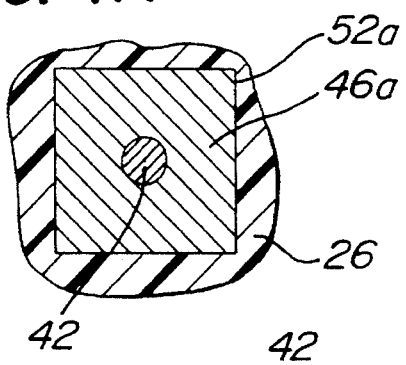
FIG. 4A is a sectional view taken along line 4A–D of FIG. 3.
Figure 4B:
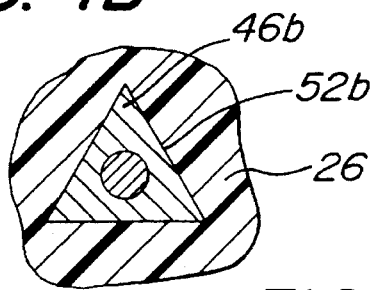
FIG. 4B is a sectional view taken along line 4A–D of FIG. 3.
Figure 4C:
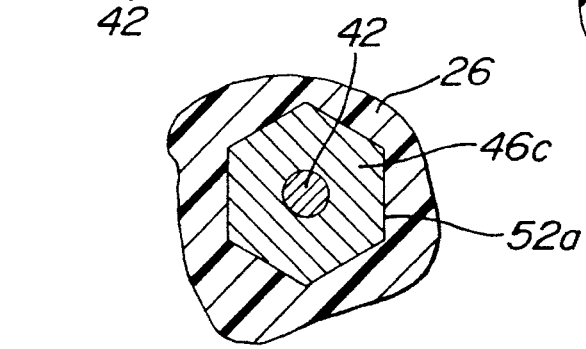
FIG. 4C is a sectional view taken along line 4A–D of FIG. 3.
Figure 4D:
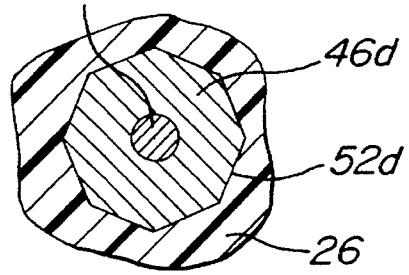
FIG. 4D is a sectional view taken along line 4A–D of FIG. 3.

In addition, dental implants in general may have a variety of anti-rotational coupling shapes. These shapes are shown in FIGS. 4A–4D. In particular, FIG. 4A shows a square anti-rotational coupling 46a, whereas FIG. 4B shows a triangular anti-rotational coupling 46b, FIG. 4C shows a hexagonal anti-rotational coupling 46c, and FIG. 4D shows an octagonal anti-rotational coupling 46d. As such, the insert 26 that will be selected to engage a particular dental implant secured in the patient's jaw will have a mating anti-rotational coupling 52a, 52b, 52c or 52d, respectively. Therefore, the plastic inserts which have been designed herein can fit any male or female anti-rotational configuration on the head of a dental implant and can be altered to fit any future design.

The insert 26 is itself releasably secured within the healing cap housing 24. To that end, the insert 26 has a retentive lip 56 (FIGS. 2–3) that runs along the distal side 58 of the insert 26 and a retentive lip 60 (FIG. 3) that runs along the mesial side 62 of the insert 26. The housing 24 includes a lower chamber 64. When the insert 26 is pressed far enough into the lower chamber 64, the retentive lips 56 and 60 lock into retentive grooves 66 and 68, respectively, which are milled along the inside distal wall 70 and the inside mesial wall 72, respectively of the housing 24. This action snap-fits the insert into the housing.

Figure 3:
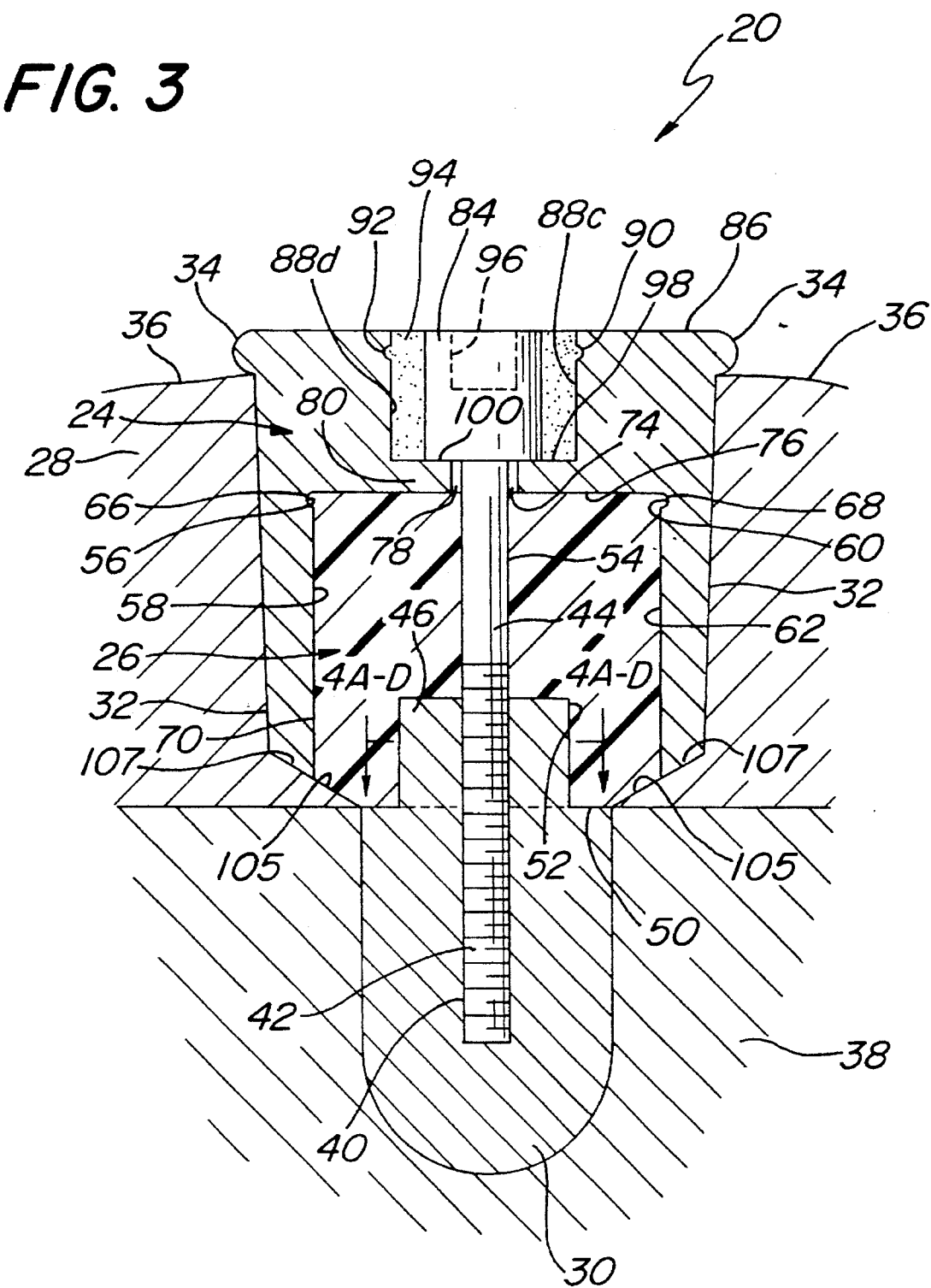
FIG. 3 is an enlarged sectional view taken along line 3—3 of FIG. 1.

With the insert 26 locked into the housing 24, the opening 74 (on the insert's 26 top surface 76) to the central insert bore 54 is aligned with a central opening 78 in an intermediate wall 80 of the housing 24, which will be discussed in detail later. The retaining screw 44 is then passed down through the opening 78 and down through the central insert bore 54 where the threaded end 42 is screwed into the dental implant bore 40. As can be seen in FIGS. 2 and 3, only the plastic insert 26 of the healing cap 20 is in contact with the head 50 and the anti-rotational coupling 46 of the implant 30.

Furthermore, for dental implants 30 having a female coupling utilizing a "Moore's" tapered circular design, the insert 26 has a corresponding male coupling to lock into the implant's 30 Moore's taper.

As can be seen in FIGS. 2–3, the housing 24 also has an upper chamber 82 that houses the head 84 of the retaining screw 44. The purpose of the chamber 82 is to ensure that head 84 does not project upward beyond the top surface 86 of the housing 24 but rather remains recessed within the housing 24 during securement of the healing cap 20 to the dental implant 30. A light curable filler 94 is provided within the chamber 82 after the retaining screw 44 has been tightened, as will be described later. As can be seen in the occlusal view of FIG. 1, the chamber 82 has a rectangular shape, having a buccal wall 88a, a lingual wall 88b, a mesial wall 88c and a distal wall 88d. A groove 90 is milled along the distal wall 88c and another groove 92 is milled along the mesial wall 88d. The purpose of these grooves is to provide recesses into which the light-curable filler 94 can flow and harden, thereby securing the hardened filler within the chamber 82. The filler 94 serves to close off the chamber 82 so that the top edge 86 of the housing 24 forms a smooth flat surface precluding penetration of material, e.g., foreign particles, during second stage healing when the healing cap 20 is secured within the patient's mouth. As shown in FIG. 1, the filler 94 even penetrates the slot opening 96 in the retaining screw's head 84 and fills that slot. The slot 96 had previously served to receive the driver device, e.g., screwdriver, (not shown) to lock the retaining screw 44 down into the dental implant 30. Note that the filler grooves 90 and 92 run in the same direction that the retentive grooves 66 and 68 run in the lower chamber 64 of the housing 24. This orientation facilitates the machining of the housing 24 by permitting the milling machine to run in one direction to create both the filler grooves and retentive grooves.

Figure 2A:
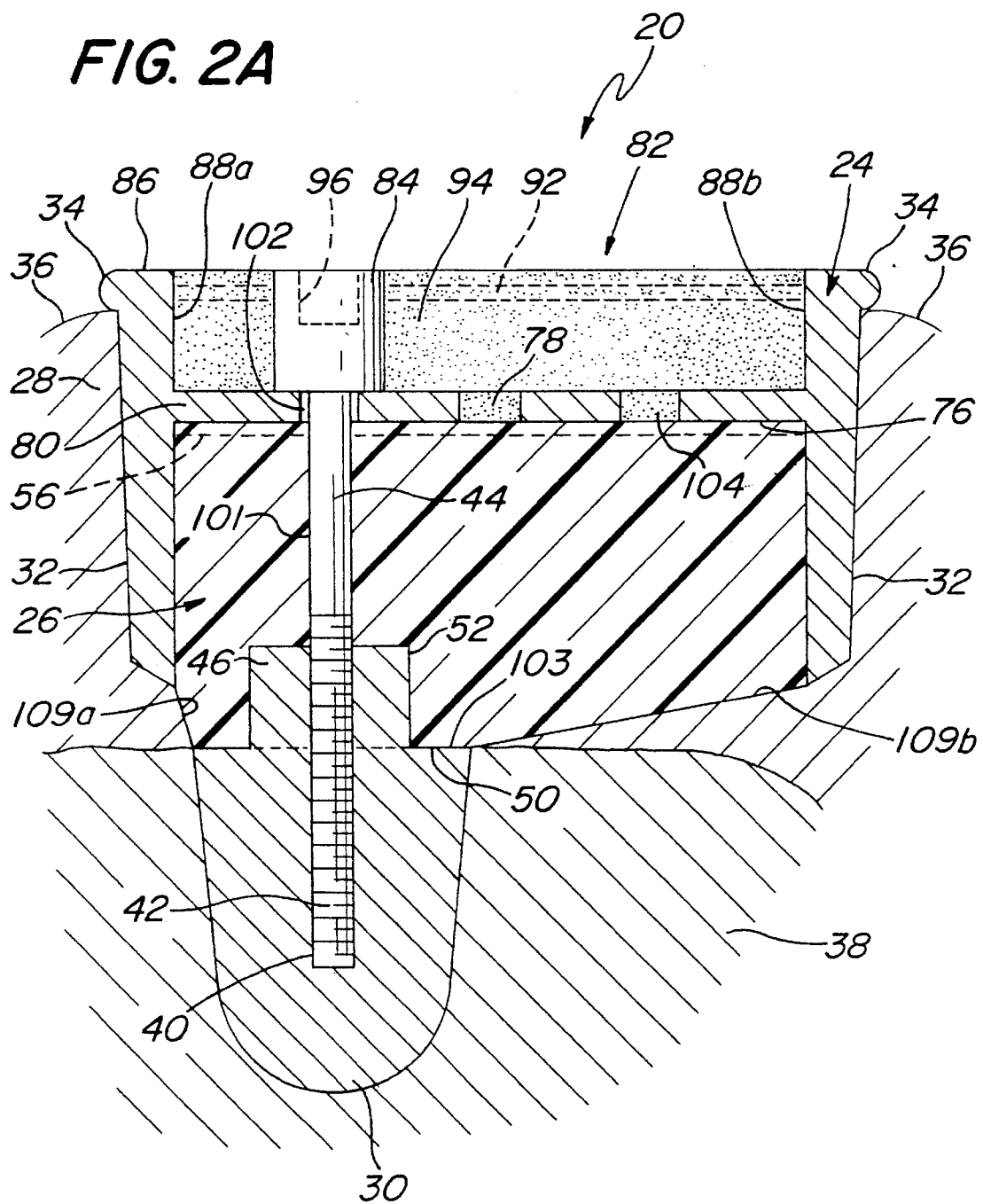
FIG. 2A is a view similar to that of FIG. 2 but showing use of a different insert.

As can be seen in FIG. 2, the bottom of the upper chamber 82 is formed by the upper surface 98 of the intermediate wall 80. The bottom surface 100 of the screw's head 84 is tightened against the upper surface 98 in order to lock the healing cap 20 onto the head 50 of the dental implant 30. The intermediate wall 80 has three circular openings in it, namely, a buccal opening 102, the heretofore mentioned central opening 78 and a lingual opening 104. The upper chamber 82 is of rectangular shape and includes the openings 102, 78 and 104 to provide the surgeon with ability to secure the healing cap 20 to a dental implant 30 which was implanted off-center of the normal first bicuspid tooth 22, without having to move the healing cap 20 in order to align the cap 20 with the head 50 of the implant 30. As will be appreciated by those skilled in the art, implants are frequently off-center since the quantity of bone does not always allow the surgeon to drill a centered implant hole. Thus, the surgeon may have no choice but to drill to an off-center location. The healing cap of this invention accommodates off-centered implants (for posterior teeth only). For example, if the dental implant 30 is implanted in the jawbone at a more buccal location, such as shown in FIG. 2A, then the surgeon should select an insert 26 having a buccal bore 101 and should snap-fit that insert 26 into the lower chamber 64 to align that bore 101 with the buccal opening 102 and thereby receive the buccally located implant 30. If the dental implant 30 is implanted in the jawbone at a more lingual location, i.e., to a position more towards the right of where the implant 30 is drawn in FIG. 2, then the surgeon should select an insert 26 having a lingual bore (not shown) that aligns with the lingual opening 104. In the exemplary embodiment of FIGS. 1–3, the insert 26 that has a central bore 54 to align with the central opening 78.

In order to imitate the natural curvature of the cavity 32 in the gingiva, the bottom surface 103 of each insert 26 is tapered at the edges 105 so that the bottom surface 103 is in contact with either the head 50 of the implant 30 or the gingiva tissue 28 only. No part of the jawbone 38 is to be in contact with the healing cap 20 and as such even the housing 24 has tapered edges 107. This tapering will be imitated when the crown is being created, as will be discussed later.

Where a buccal core 101 insert is used, the taper 105 will not be symmetrical, as depicted in FIG. 2A, due to the orientation of the bottom surface 103 with respect to the head 50 of the implant 30. In particular, the tapered edge 109a will be steeper for the taper closer to the head 50 of the implant 30 and shallower for the tapered edge 109b further away from the head 50 of the implant 30. For a lingual core insert (not shown), the tapered edges 109a and 109b will be reversed.

Because the selected insert 26 has only one bore that aligns with either the buccal opening 102, the central opening 78 or the lingual opening 104 in the intermediate wall 80, when the light curable filler 94 is poured into the upper chamber 82, the unused openings will be filled with filler 94, as can be seen in FIG. 2. (In that figure, the buccal opening 102 and lingual opening 104 are closed off by the top surface 76 of the insert 26 which traps the filler 94 in those openings).

It is also important to note that the buccal opening 102, central opening 78 and lingual opening 104 in the intermediate wall 80 are all of the same diameter and are larger than the opening 74 forming the entrance to the central bore 54 (or the opening forming the entrance to buccal bore 101 or the opening forming the entrance to the lingual bore) in the insert 26. This construction enables one to later remove the insert 26 from the housing 24. In particular, an insert removal punch (not shown) is used to push the insert 26 out of the housing 24 so that the insert 26 can be disposed of and the housing 24 reused after the healing cap 20 has been removed from the patient and the retaining screw 44 removed. The punch has a tip (not shown) that is inserted through the particular opening 102, 78 or 104 opening and down into the opening in the bore in the insert 26. The tip forcibly engages the plastic walls of the insert bore and after an impulse pressure is applied to the punch, the retentive lips 56 and 60 will be disengaged from their respective retentive grooves 66 and 68, thereby dislodging the insert 26 from the reusable housing 24. It is preferable that the punch be of an autoclavable material to withstand frequent sterilizations.

The other posterior healing cap 20 categories, i.e., Category V (FIG. 10) and Category VI (FIG. 11) operate in the same fashion.

An example of the wide adaptability of the present invention is as follows: if the surgeon was putting in three lower implants 30 in a row for the second molar, first molar, and second bicuspid and the first molar implant was several millimeters lingual to the straight arch-form needed for alignment, the surgeon would select a Category VI healing cap 20 for the second molar, using an insert 26 with a center bore 54. The surgeon would also select a Category VI healing cap 20 for the first molar using an insert 26 with a lingual bore (because the implant head 50 is several millimeters lingual). The surgeon would also select a Category IV healing cap 20 for the second bicuspid using an insert 26 with a center bore 54. Hence, all the posterior healing caps 20 would be aligned in the proper arch formation because the insert 26 selected for the first molar healing cap 20 compensates for its respective dental implant 30 being more lingual rather than on-center.

Figure 5:
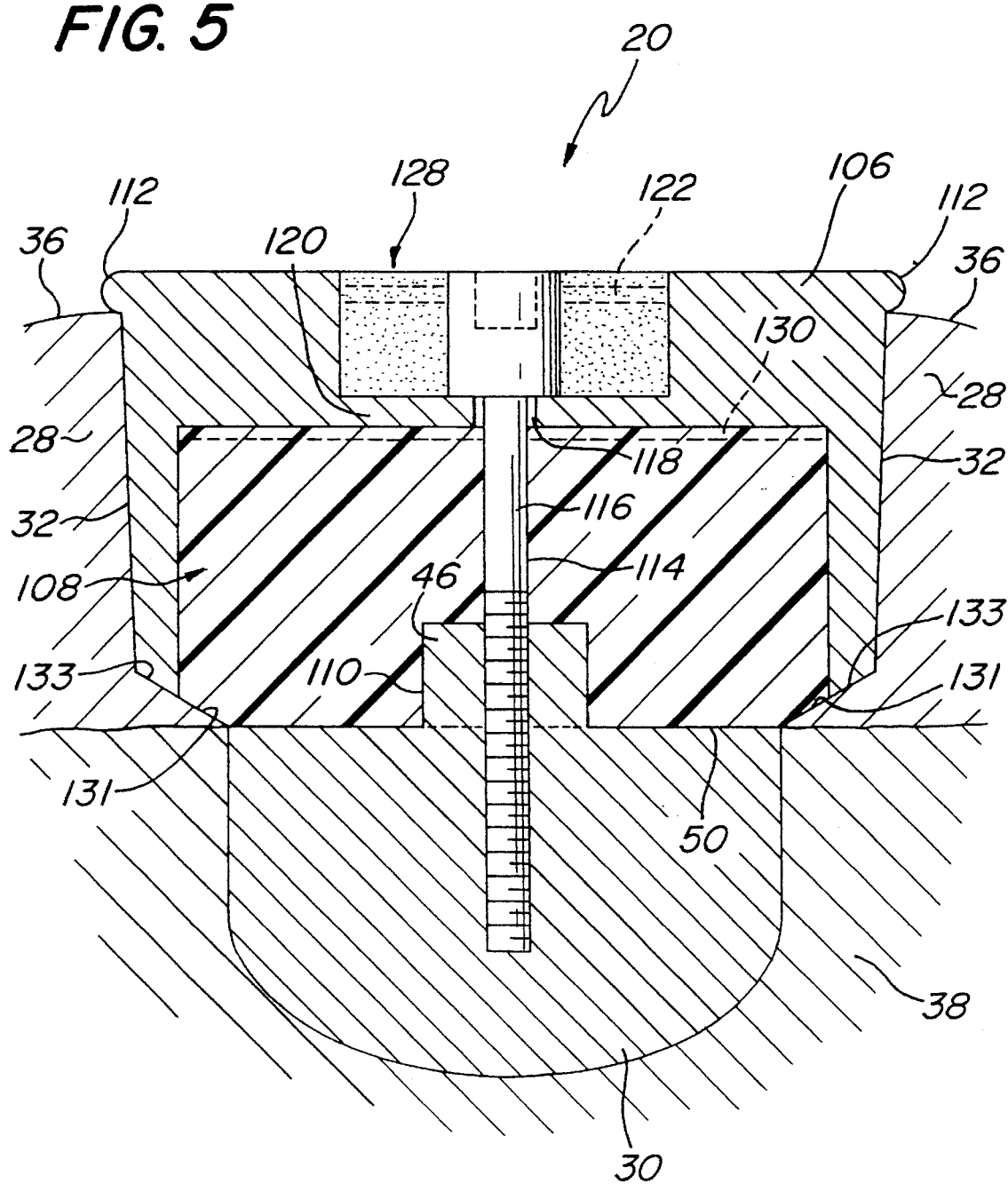
FIG. 5 is a view like that of FIG. 2 but showing an anterior healing cap inserted in the lower jaw.

A healing cap 20 for an anterior tooth is shown in FIG. 5. Therefore, the structure of Category I (FIG. 7), Category II (FIG. 8), Category III (FIG. 9) and Category VII (FIG. 12) healing caps 20 can be discussed with reference to FIG. 5. Anterior healing caps 20 also comprise a titanium housing 106 and a plastic insert 108. The housing 106 is preferably formed of a reusable titanium material, whereas the insert 108 is preferably formed of plastic and is disposable. Moreover, the anti-rotational coupling 110 of the insert 108 can take the form of a male or female coupling having a square, triangular, hexagonal or octagonal shape depending upon the type of dental implant 30, as discussed earlier regarding posterior healing cap inserts 26. In addition, all anterior healing caps 20 have an occlusal lip 112 which serves the same purpose as discussed earlier.

However, unlike the posterior healing cap inserts 26, all anterior healing cap inserts 26 have only a central bore 114 through which the retaining screw 116 passes in order to secure the healing cap 20 to the implant 30. Consequently, there is only one opening 118 in the intermediate wall 120 of the housing 106 of an anterior healing cap 20. The reason for this is that the size of anterior healing caps 20 (Categories I–III, VII) do not allow for any off-center securement as was available for the posterior healing caps 20.

Furthermore, the small size of anterior healing caps 20 also requires that the filler grooves (only one, 122, of which is depicted in FIG. 5) run along the lingual 124 and buccal 126 walls (FIGS. 7–9, 12) of the upper chamber 128, rather than along the mesial and distal walls as in the posterior healing caps 20. Similarly, the retentive grooves (only one, 130, of which is depicted in FIG. 5) run along the lingual and buccal inner sides of the housing 106 rather than the along the mesial and distal walls as in the posterior healing cap housings 24.

As with the posterior healing caps 20, the inserts 26 for anterior healing caps 20 also have tapered bottom edges 131 and the housings 24 also have tapered edges 133 for the same reasons discussed earlier.

In addition, to prevent the top edge of the anterior healing caps 20 from obstructing tongue movement, the top edge of the lingual side is tapered. In particular, lingual edge surfaces 132 (Category I, FIG. 7), 134 (Category II, FIG. 8), 136 (Category III, FIG. 9 and 138 (Category VII, FIG. 12) are tapered, i.e, they are canted downward into the page, away from the plane containing the opening to the upper milled chamber 128.

As discussed earlier with respect to posterior healing caps 20, the housings 106 of anterior healing caps 20 have predetermined crucial dimensions corresponding to at least the mesio-distal dimension and the labio-lingual dimension, as set forth in Tables A and B.

In order to minimize the misalignment of the dental implant 30 before it is permanently implanted in the jawbone 38, the system of the subject invention not only includes the heretofore discussed healing caps 20 but also two pre-surgery devices, namely, plastic dowels and an implant alignment indicator 140.

The plastic dowels are solid plastic replicas of the Category I–VII healing cap housings 24 and 106, i.e., the dowels are of the same anatomical size and dimensional shape as their respective healing cap housings 24 and 106. These dowels are to be used at the outset by the dentist for initially locating where the dental implant 30 will be secured. Because the doctor will want to be able to verify any proposed location of an implant 30, it necessary to make a model of the dowel which the dentist can cut into, mark up, etc. in order to finalize the implant location. The dowel itself is not to be altered.

Initially, an upper and lower study model is taken of the patient's teeth by the dentist. The doctor then sends these models to the laboratory. The technician simply picks a particular dowel (e.g., a bicuspid, molar, or canine dowel), and releasably secures it to the study model by way of an adhesive (e.g., using a "fillet activator", which is a glue that hardens by spraying a liquid to it). The dowel can then be positioned in the proper arch formation in the study model to designate the area where an implant 30 will be placed.

Creating a model of the dowels is as follows: after the dowels are secured to the model, a vacuum pressed plastic stint (not shown) is made. The stint is trimmed and removed as usual and the dowel can be removed from the stone model and returned. The stint will now have dowel impressions. The dowel impressions in the stint will be filled with a clear acrylic which hardens. After the acrylic hardens, the dowel impressions are removed from the stint. These "models of the dowels" can then be placed back on the study model and cured, and sent to the surgeon or periodontist in charge of the surgery. They now have an accurate representation of where the healing cap 20 can be placed. Since the dowel and the healing cap 20 are of the same anatomical dimensions of the natural teeth being replaced, the overall view of the proper anatomy design is increased.

The implant alignment indicator 140 is shown in FIG. 6 and serves to facilitate the alignment of the implant before it is permanently secured. The indicator 140 basically comprises an elongated shaft having a male or female tip at the distal end of the shaft. The tip is constructed to mate with the anti-rotational coupling of the implant. The proximal end of the indicator 140 comprises a pair of cross members 142 and 144 which are disposed perpendicularly to each other and to the longitudinal axis of the shaft. These members provide alignment cues in the buccal-lingual directions and the mesial-distal directions, respectively. In particular, after the site for the dental implant 30 has been selected and the surgeon is preparing to permanently tighten the dental implant 30 into the bone 38, the surgeon preferably engages the implant alignment indicator 140 with the anti-rotational coupling 46 of the implant 30. The surgeon then sights down at the cross members 142 and 144 to ascertain whether the implant 30 needs to be rotated any further down into the bone 38 to ensure that the healing cap 20 will be oriented correctly when it is engaged with the implant head 50. This will, in turn, assure proper alignment in arch-form with surrounding teeth. In addition, the indicator 140 allows the surgeon to visualize the attitude of the healing cap 20 when it resting on the implant 30. The attitude of the healing cap 20 will determine how the surrounding gingiva tissue 28 will heal around the healing cap 20, thereby establishing how the crown will emerge from the crater 32. Therefore, the alignment indicator 140 assures the surgeon whether there is proper arch alignment and proper angulations of the gingiva tissue emergence. Furthermore, the surgeon can at this point, also determine if a soft tissue graft will be necessary to ensure the proper angulations. If there is not enough soft tissue to establish the proper angulation, the surgeon can schedule a graft operation to be at the next stage, thereby avoiding a later surgery just to accomplish the graft.

The alignment tool 140 can be used differently depending on the type of dental implant 30 used. For example, if the dental implant 30 to be used is a press fit, then as the dental implant 30 is being inserted into the bone 38, the surgeon will stop at least half way down (i.e., before the dental implant is finally seated) and engage the alignment tool 140 into the dental implant head 50. The surgeon will then check the buccal-lingual-mesial-distal alignment with respect to surrounding teeth and thereby make any necessary rotation of the dental implant 30 to correct the alignment. Once this is accomplished, the surgeon will then press down and thereby fully insert the dental implant 30 down into the bone 38.

If the dental implant 30 is a screw-down type, the nominal depth of a bore that is burred, i.e., drilled, in the bone 38 for dental implant 30 insertion is approximately 11 mm. The dental implant 30 is then screwed down into the bore until the 10.125 mm depth point is reached. At that point, the alignment indicator 140 is engaged into the head of the implant 30. The surgeon will then check the buccal-lingual-mesial-distal alignment and, if there is any need to rotate the implant 30 to correct for alignment, the remaining 0.875 mm will permit further rotation of the implant 30. The reason for not bottoming out the implant 30 to the bore bottom is that once a dental implant 30 is tightened down into the bone, the surgeon can not back out the implant 30 or else the implant 30 securement will be compromised.

If more than one dental implant 30 is to be implanted, an alignment indicator 140 should be provided for each implant 30 to verify the alignment thereof.

As should be appreciated by those skilled in the art, after the three weeks of healing has been completed with any type of healing cap in place, the patient has his/her stitches removed and is ready for the restorative doctor. When an anatomically correctly shaped healing cap 20 of this invention is used and has been in place for the three weeks, the proper emergence diameter of a naturally formed tooth will remain in the gingiva tissue when the healing cap 20 is removed at this time. What remains in the patient's jaw is a natural tooth cavity 32 (FIG. 13) in the gingiva tissue 28 with the head 50 of the implant 30 visible at the bottom of this cavity 32.

Figure 13:
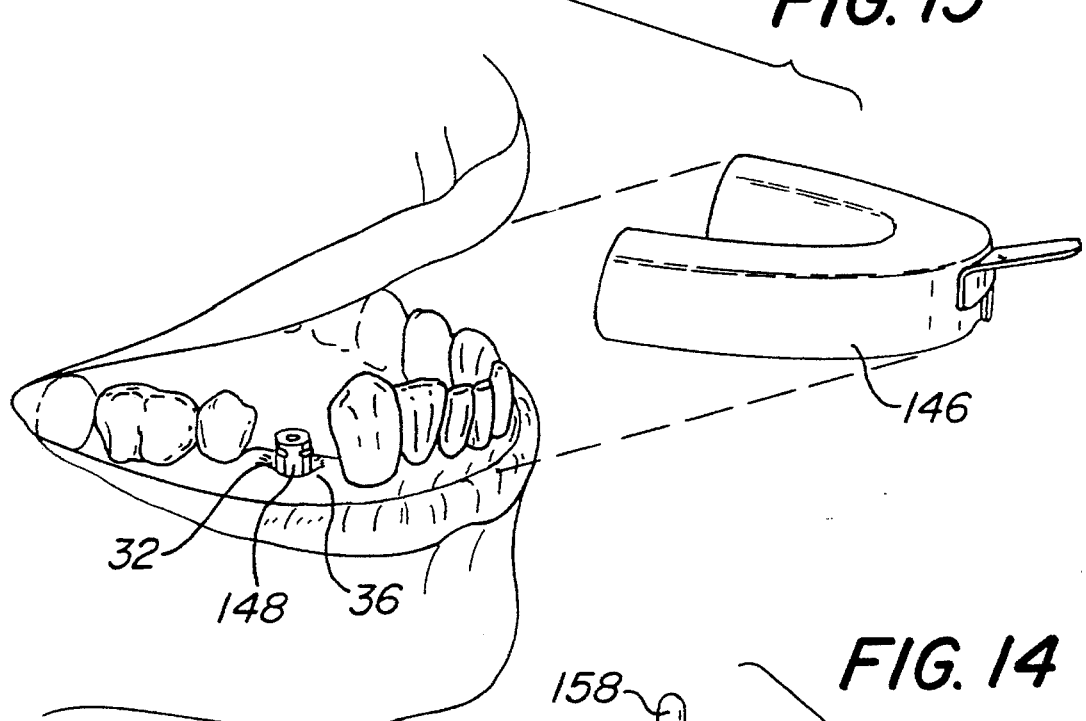
FIG. 13 is an isometric view of the mouth of a patient after the healing cap of this invention has been used to create an appropriately shaped anatomical cavity for a crown and showing the initial step in the making of an impression for the crown.

In accordance with standard practice, the restorative doctor takes a transfer impression 146 of the jaw which contained the healing cap 20. The transfer impression 146 basically comprises a holder with an unset mold material 150 therein that is press-fit over the teeth. This unset mold material enables an impression to be made of the teeth in the appropriate jaw. In order to preserve the opening and position of the head 50 of the implant 30, a cylindrical impression post 148 is engaged with the implant 30 in the patient's mouth as shown in FIG. 13. The transfer impression 146 is then made. Because the cavity 32 established in the patient's gingiva 28 has the natural shape of the tooth, with the subject invention there is no need to use a convention retraction cord which is typically used to substantiate the depth of the head 50 of the implant 30, i.e., a conventional cylindrical healing cap would establish a narrow cylindrical passageway through the gingiva tissue 28 leading to the head 50 of the implant 30. In particular, using the prior art the dentist would have to insert a retraction cord to force open the passageway to enable access to the head 50 of the implant 30 during securement of the crown to the implant 30, as will be discussed later.

Figure 14:
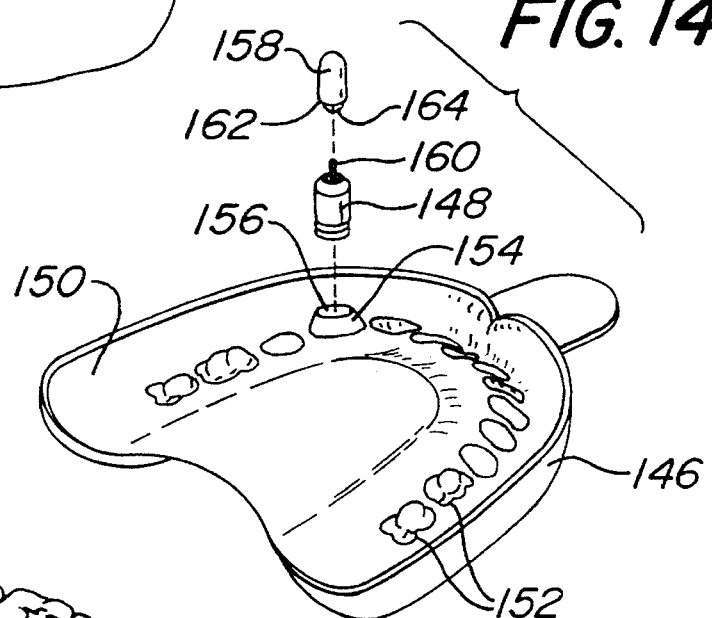
FIG. 14 is an exploded isometric view of various components used to make a dental mold, i.e., stone model, for the crown.

When the transfer impression 146 is removed and inverted (as shown in FIG. 14), the now set mold material transfer impression 150 will have teeth impressions 152 and an anatomically-correct cavity impression 154 therein. The cavity impression 154 has an entrance (top) hole 156 being the diameter of the cylindrical impression post 148 that was engaged with the implant 30. Therefore, this cavity impression 154 is an anatomically correct representation of the cavity 32, from the head 50 of the implant 30 to the gingiva crest 36. Once the impression is completed, the impression post 148 is disengaged from the implant 30. The healing cap 20 is then reinserted and secured to the implant 30 in the cavity 32 in the patient's gingiva 28.

The dentist then sends the transfer impression 146, the impression post 148 and other related items (e.g., the patient's wax bite and counter model) to the dental laboratory to make the stone model so that the crown can be made. To that end, the laboratory takes the impression post 148, inverts it and then reinserts it into the cavity impression 154. An implant analog 158 is then engaged on the free end 160 of the impression post 148. The implant analog 158 is replica of the implant 30, including a head 162 and an anti-rotational coupling 164 that is identical to the respective head 50 and anti-rotational coupling 46 of the implant 30 and is ordered from the manufacturer of the dental implant 30.

Figure 15:
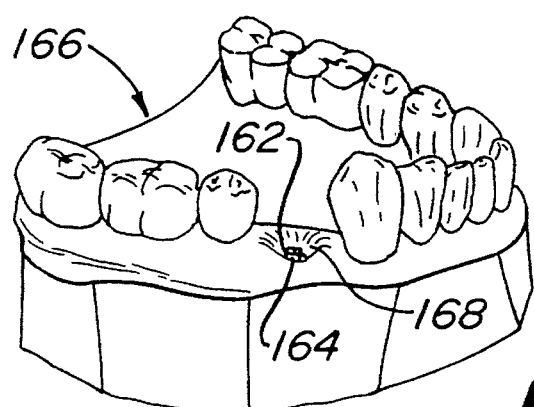
FIG. 15 is an isometric view of the stone model made from the impression mold.

The laboratory uses the transfer impression and the impression post to prepare the stone model 166, which is shown in FIG. 15. This model precisely replicates the anatomically correct cavity 32, the head 50 and anti-rotational coupling 46 of the implant 30 (which is permanently secured in the patient's jaw). The stone model 166, therefore, includes an anatomically correct cavity 168 at the location of the tooth to be replicated. The cavity 168 has the dental implant analog 158 embedded in it. The analog 158 has a head 162 and anti-rotational coupling 164 which are located at the bottom of the cavity 168.

In addition, the inwardly tapered cavity impression 154 helps to stabilize the inverted impression post 148 in the transfer impression mold 15, unlike the typical narrow cylindrical "tube" shape that is left in the transfer impression mold 150 by conventional cylindrical healing caps. By stabilizing the inverted impression post 148, the cavity impression 154 prevents the post 148 from shifting slightly or disengaging from the impression mold 150 altogether during the transfer action. As can be appreciated by one skilled in the art, any slight movement of the impression post 148 within the transfer impression mold material 150 during transfer will degrade the replication of the cavity 32. Hence, when the stone model 166 is eventually made from the transfer impression 146, the model 166 will not be accurate, so that the crown created therefrom, will not align correctly when it is inserted into the cavity 32 in the patient's jaw.

After the stone model 166 is made, the technician removes the impression post 148 from the embedded implant analog 158 in the stone model 166 leaving the stone model as shown in FIG. 15. The stone model 166, now becomes the guidance platform from which the crown 170 or 170b (FIGS. 16 and 17) is made.

As should be appreciated by those skilled in the art, the use of the healing cap 20 during second stage surgery provides the following advantages over the prior art in creating the stone model 166. Firstly, if a conventional cylindrical healing cap was used during second stage healing, the resulting stone model 166 does not have an anatomically correct cavity 164 around the opening to the implant analog 158; therefore, the technician will have to actually cut away some of the stone to assist in re-inserting the impression post 148, thereby defeating the whole purpose of creating the stone model 166 in the first place. Secondly, as will be discussed later in the creation of a cementable crown, a soft tissue model must be created to anticipate the crown being pressed tightly down against the gingiva crest 36. Because the cementable crown developed under conventional methods will abut the gingival crest 36 rather than being seated deep into the gingiva tissue 28 (because there is no anatomically correct cavity 164 in the stone model 166) the soft tissue model gives the technician only an image of the opening to the gingiva tissue. The technician must still guess at the depth and width of the channel preserved in the gingiva. Use of the healing cap 20, on the other hand, preserves an anatomical crater inside the gingiva tissue so that the cementable crown seats properly therein. Thus, the technician does not have to guess as to how wide or deep the cementable crown must be created because the soft tissue model depicts the correct shape. Thirdly, use of the healing cap 20 preserves an anatomical cavity that permits sufficient room for the dentist to work within when creating the crown. Thus, there is no need to force retraction cord into the cavity preserved in the gingiva (which cord not only may damage the gingiva, but can be painful enough to the patient as to require anesthesia to be administered to patient before the retraction cord is used) to enable the dentist to ascertain crown depth and width.

Using the stone model 166, the technician can begin to form the crown. There are basically two types of crowns that can be created: a screw-down type and a cementable type. In most cases, the type of crown to be made is determined by the type of implant 30 used in with the patient. The different processes used in creating these crowns will be discussed briefly later. Suffice it to say for now that a screw-down type comprises one piece having a hole in the top that allows a retaining screw to be passed down through it to engage the implant 30. A cementable crown comprises two parts, a base and a cementable shell. The base of the cementable crown is secured to the implant 30 and then later the cementable shell is secured to the base. Both types of crowns require that a crown substructure, known as a "prepped tooth" be created initially.

As is known, a prepped tooth has a restorative castable cylinder (sometimes referred to as "RCC" or an "abutment") 172. The abutment or RCC provides the securement means of the crown to the dental implant.

Figure 16:
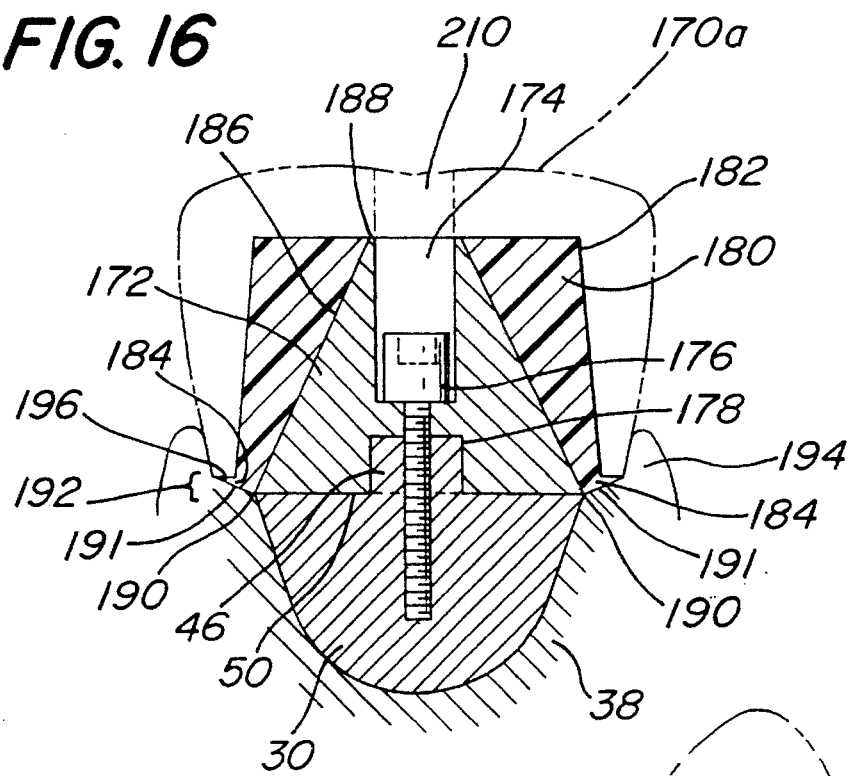
FIG. 16 is a vertical sectional view of a prepped tooth portion of a crown using a burnout sleeve constructed in accordance with one aspect of this invention.
Figure 17:
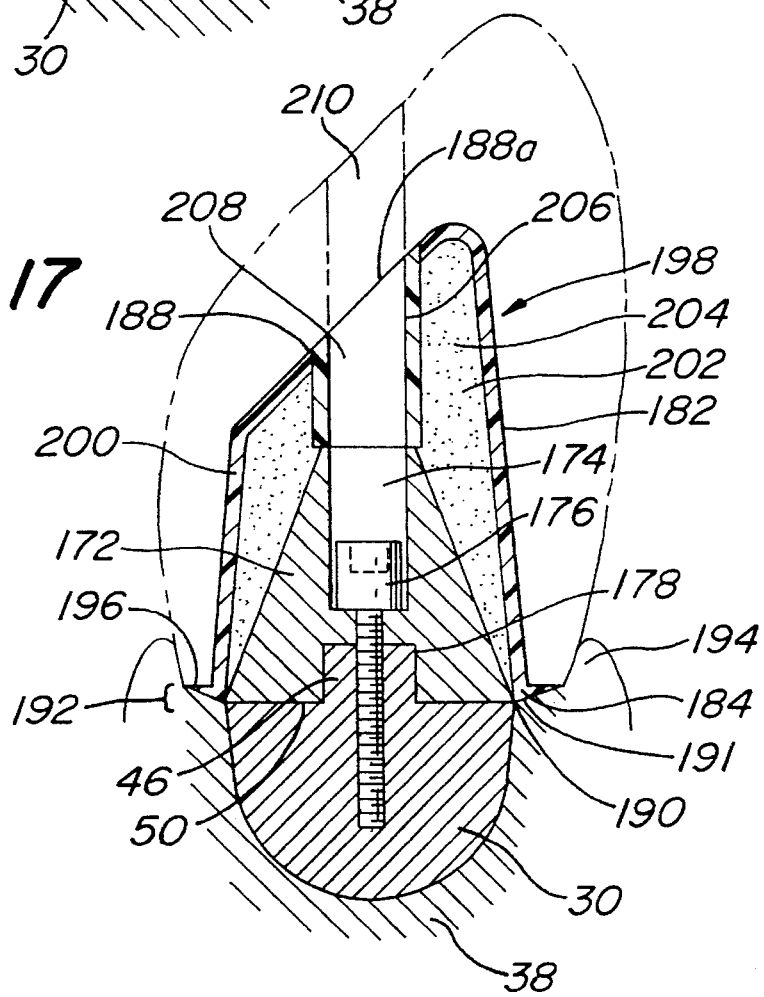
FIG. 17 is a view similar to FIG. 16 but showing another burnout sleeve constructed in accordance with another aspect of this invention.

In FIGS. 16 and 17 two exemplary crowns 170a (a molar crown) and 170b (a bicuspid crown), respectively, are shown being constructed using the teachings of this invention. Each crown includes an abutment 172 which, as is conventional, can vary in shape and size. However, the RCC 172 comprises a bore 174 to allow for the passage of a retaining screw 176. The RCC 172 also has a mating male or female coupling 178 that engages the anti-rotational coupling 46 of the implant 30. The RCC 172 is the platform about which the crown 170a or 170b will be built, i.e., the stump to which the crown is attached. Typically, the dental technician then begins to "wax" the RCC and then to sculpt a prepped tooth from the surface of the RCC 172.

In accordance with another aspect of this invention, the system of this invention includes means to facilitate the fabrication of a perfectly prepped tooth. That means comprises in one instance a plastic burn-out sleeve 180 (FIG. 16). This sleeve is arranged to slide over the RCC 172. The burn-out sleeve 180 basically comprises an outside surface 182, a tapered cavity collar 184, an inner bore 186. The bore includes a top opening 188 and a bottom opening 190. The outer surface 182 of the plastic burn-out sleeve 180 is designed to correspond to the dimensions of a naturally prepped tooth. The cavity collar 184 includes a side surface which extends about the entire periphery of the outer surface 182 and forms the lower portion of the cavity 32. This ensures that the crown is created with the same anatomical dimensions that the particular tooth exhibited in the gingiva tissue at that particular location.

The burn-out sleeve 180 is placed on the RCC 172 so that the RCC resides within the bore 186. The technician then secures ("loots") these two pieces together with hot wax.

The tapered cavity collar 184 is selected to be of a sufficient thickness 192 necessary to support the crown 170a or 170b thereon. The collar also should exhibit the proper cusp formation 194 to ensure proper tooth emergence profile with the surrounding gingiva 28. To that end, the collar 184 is in the form of an annular flange extending around the entire periphery of the burn-out sleeve 180. The cavity collar 184 includes a planar top surface which acts as the stop surface or support for both the acrylic temporary crown (cementable type crowns only) and the final metal construction. Among other benefits of proper emergence profile, because the crown bottom 196 fits tightly to the collar 184 with no gaps, the lack of any spaces between the crown 170a (or 170b) and the collar 184 prevents plaque from developing therebetween and eventually destroying the implant 30. On conventional crowns where the bottom surface of the crown 170a (or 170b) does not make a flush interface, any such overhangs will develop plaque, leading to degradation of the implant 30 and gingiva degeneration. Furthermore, the collar 184 is tapered 191 to match the taper 105 of the insert 26. Thus, the prepped tooth seats squarely in the cavity 32.

The system of this invention includes another burn-out sleeve for facilitating the prepping of a tooth. This other burn-out sleeve is shown in FIG. 17 and is referred to as a hollow burn-out sleeve 198. In some circumstances where the RCC 172 being used is not compatible with the plastic burn-out sleeve 180 for a particular tooth shape or where the selected insert hole is off center of the crown (e.g., a posterior healing cap 20 which has an insert 26 that utilizes a buccal bore or a lingual bore rather than the central bore 54), the hollow burn-out sleeve 198 is used. The hollow burn-out sleeve 198 is constructed so that its outer surface 182 and cavity collar 184 are the same as in the burn-out sleeve 180. However, the inside of the hollow burn-out sleeve 198 is just that, hollow. That is, the burn-out sleeve 198 does not have an inner bore 186. Instead, the burn-out sleeve 198 is a hollow, thin-walled member which is filled with wax. In particular, the sleeve comprises a thin-wall 200 (e.g., 0.5 mm) which is slipped over the top of the RCC 172 so that a gap 202 remains between the RCC 172 and the hollow burn-out sleeve 198. This gap 202 is filled with wax 204 to make the RCC 172 and the hollow burn-out sleeve 198 a solid entity. The hollow burn-out sleeve includes a central hole 188a which serves as the entry port for the wax.

As also shown in FIG. 17, should the RCC 172 selected be shorter than the hollow burn-out sleeve 198 (or a plastic burn-out sleeve 180) such that the top surface of the RCC 172 does not coincide with the top opening 188 in the hollow burn-out sleeve 198 (or a plastic burn-out sleeve 180), a hollow cylinder 206 is inserted in the central hole 188a. The open central passageway 208 in the hollow cylinder 206 preserves a pathway during the casting procedure (to be described hereinafter) for the passage of the retaining screw 176 at a later time when the crown is secured to the implant.

With the plastic burn-out sleeve 180 or hollow burnout sleeve 198 (and the hollow cylinder 206, if used) secured together, the resulting unit can then be subjected to a casting procedure to create a single metal unit, known as the prepped tooth. The contour of the outer surface 182 and angulations of the burn-out sleeve act to maintain the proper tooth contour during casting. In particular, during the casting procedure the burn-out sleeve 180 burns away and is replaced with metal (i.e., gold, titanium) which takes on the same shape of the burn-out sleeve's outer surface 182.

At this stage, the crown creation varies depending on whether a screw-down type crown or a cementable-type crown is to be created.

If a screw-down type crown is to be made, the technician engages the metal prepped tooth with the implant analog 158 in the anatomical cavity 168 in the stone model 166. Porcelain is then applied directly to the metal prepped tooth to form the crown. The applied porcelain conforms to the anatomical cavity 168 and will have a flat, horizontal bottom surface 196. Because the porcelain conforms to the cavity 168, the crown 170a or 170b will have the proper cusp formation 194. The upper portion, i.e., the portion above the top of the burn-out sleeve of the crown 170a or 170b, is then formed in the natural shape of the tooth. This natural shape is depicted by the broken line in FIGS. 16 and 17. A vertical bore 210 is maintained through the porcelain which aligns with the RCC bore 174. After the porcelain is fired and carved, the entire screw-down type crown is removed from the model 166. The healing cap 20 is then removed from the cavity 32 in the patient's mouth and the screw-down type crown is permanently secured to the implant 30 in the patient's mouth. To that end, the retaining screw 176 is passed down through the bores 210 and 174 and secured into the implant 30. A light curable filler material (not shown) is then poured into the bores 210 and 174 to close off those channels and then cured to set.

If a cementable-type crown is to be made, a plastic temporary crown (not shown) is first made to secure positioning of the emergence tissue 32 created by the healing cap 20 for the loading period (e.g., three to four months) suggested by the dentist before a permanent cementable crown is inserted. This "temporary" crown is necessary for soft-loading the implant 30 in the bone 38. The temporary crown is created by engaging the metal prepped tooth into the anatomical cavity 168 and then pouring an acrylic around the metal prepped tooth and in the cavity 168. The acrylic temporary crown, therefore, has an appropriately shaped outer surface (shown by the broken lines in FIGS. 16 and 17). The inside surface of the temporary crown has a shape corresponding to the prepped tooth that is in the patient's mouth.

The temporary crown is then removed from the prepped tooth and the prepped tooth is removed from the model 166. Next, the metal prepped tooth is secured to the implant 30 in the patient after the healing cap 20 is removed. In particular, the retaining screw 176 is passed down through the bore 174 (and passageway 208, if a hollow cylinder 206 was used in the prepped tooth) to be permanently secured in the central bore 40 of the implant 30. Therefore, there is no need for a bore 210 through the porcelain cementable crown. Cement is then applied to the inside surface of the temporary crown and the temporary crown is then cemented to the metal prepped tooth. The patient is released for the loading period.

After that time has elapsed, the doctor recalls the patient and prepares the permanent cementable crown. To that end, the temporary crown is removed to expose the metal prepped tooth. Another impression (not shown) is then taken of the cavity 32 with the metal prepped tooth in the center of the cavity 32. This is accomplished by syringing impression material around the metal prepped tooth and in the cavity 32. No retraction cord is needed because the cavity has been preserved. The temporary crown is again cemented back to the metal prepped tooth in the patient's mouth until the permanent crown is created. Another stone model, known as a soft tissue model is created. This model has the shape of the anatomical cavity 32 with the metal prepped tooth in the center, and is used to create the permanent cementable crown. The permanent crown has a metal substructure which corresponds to the metal prepped tooth. Porcelain is then applied to the metal substructure in the crown shape. The temporary crown is then removed from the metal prepped tooth and the permanent crown is then permanently cemented on the top of the metal prepped tooth.

It should be noted at this point that the above discussion concerned the creation of a single crown. However, this discussion is by way of example and not limitation and applies to the creation of a bridge (more than a single crown).

To assist the dental laboratory in creating either the cementable or screw-down type of crown using the plastic burn-out sleeves 180/hollow burn-out sleeves 198 and hollow cylinders 206, a laboratory kit (not shown), embodying at least a portion of the system of this invention, can be provided to the dental technicians. This kit may contain plastic burn-out sleeves 180, hollow burn-out sleeves 198, hollow cylinders 206 and healing cap dowels or any other future configurations.

To assist the dental surgeon in preparing the implantation of the dental implant and the insertion of the healing caps 20, a surgery kit (not shown) embodying at least a portion of the system of this invention can be provided for the surgeon. The surgery kit may comprise an entire set of Category I–VII healing caps 20, i.e., housings 24 and a variety of corresponding inserts 26 having either male or female, square, triangular, hexagonal or octagonal anti-rotational couplings, including inserts 26 having either a buccal core, a central core or a lingual core, or any other future configuration. There will also be an adequate supply of alignment indicators 140 and an insert removal punch.

It will be important that the surgeon requests a kit corresponding to the type of implants his/her office uses, due to the fact that these kits will need to be stocked with an adequate supply of healing caps 20, inserts 26, alignment indicators 140 and an insert removing punch. These kits will most likely be made with parts to engage only two different types of implants 30. Because these parts will adequately fit any present or future implant 30 designs, a refill order or purchase order will not be limited to two standard types.

Without further elaboration, the foregoing will so fully illustrate my invention that others may, by applying current or future knowledge, readily adopt the same for use under various conditions of service.

TABLE A

MAXILLARY (UPPER) HEALING CAPS/TEETH (all units are in millimeters)

| Anterior or Posterior | Healing Cap Category | Teeth (left and right) | Lenght Overall | Lenght of Crown | Mesiodistal Crown | Labiolingual Crown | * Mesiodistal Neck | * Labiolingual Neck |
|---|---|---|---|---|---|---|---|---|
| Anterior | I | Central | 25.5 | 11.3 | 9 | 7.8 | 6.5 | 7 |
| Anterior | II | Lateral | 22.5 | 10.1 | 7 | 6.7 | 5 | 6.3 |
| Anterior | III | Cuspid | 29 | 11.4 | 8.4 | 8.8 | 6 | 8 |
| Posterior | IV | 1 Bicuspid | 22.5 | 9.3 | 7.5 | 9.7 | 5.3 | 8.7 |
|  |  | 2 Bicuspid | 22.2 | 8.8 | 7.2 | 9.5 | 5.3 | 8.8 |
| Posterior | V | 1 Molar | 21.5 | 8 | 11.3 | 11.8 | 8 | 11 |
|  |  | 2 Molar | 20.5 | 7.8 | 10 | 11.5 | 7.5 | 10.5 |
|  |  | 3 Molar | 18.5 | 7.5 | 9.8 | 11.2 | 7.5 | 10.4 |

TABLE B

MANDIBULAR (LOWER) HEALING CAPS/TEETH (all units are in millimeters)

| Anterior or Posterior | Healing Cap Category | Teeth (left and right) | Lenght Overall | Lenght of Crown | Mesiodistal Crown | Labiolingual Crown | * Mesiodistal Neck | * Labiolingual Neck |
|---|---|---|---|---|---|---|---|---|
| Anterior | VII | Central | 22 | 10 | 6 | 6.3 | 3.8 | 5.7 |
|  |  | Lateral | 24 | 10.6 | 6.5 | 6.7 | 4 | 6.3 |
| Anterior | III | Cuspid | 29 | 11.5 | 7.3 | 8.3 | 5.5 | 8 |
| Posterior | IV | 1 Bicuspid | 24 | 9.5 | 7.8 | 8.5 | 5 | 7.3 |
|  |  | 2 Bicuspid | 24 | 9 | 7.8 | 9 | 5.2 | 7.7 |
| Posterior | VI | 1 Molar | 22 | 8.2 | 11.9 | 10.8 | 9.2 | 9.5 |
|  |  | 2 Molar | 21 | 8 | 11 | 10.3 | 9.2 | 9 |
|  |  | 3 Molar | 19 | 7.5 | 10.7 | 10 | 8.7 | 9 |

I claim:

1. A healing cap to be used in a predetermined position in the gingiva tissue of a patient during second stage surgery of a dental implant for mounting a crown replicating a tooth naturally residing at the position, the implant having a head with an anti-rotational coupling, said healing cap forming a cavity in the gingiva tissue, when installed in a patient's mouth whose shape replicates a portion of the tooth and comprising a housing and an insert, said housing having an outer surface including portions having at least two predetermined dimensions, said dimensions comprising the mesio-distal dimension of the neck of the tooth and the labio-lingual dimension of the neck of the tooth, said dimensions being representative of the anatomical dimensions of the corresponding portions of the tooth which was located within the gingiva tissue, said insert having coupling means to engage and mate with the anti-rotational coupling on the head of the dental implant, the anti-rotational coupling forming the opening to a threaded bore, said insert being releasably secured inside said housing by a securement means, said housing, said coupling means being adapted to be aligned with the anti-rotational coupling of the dental implant and further comprising a retaining screw passing through said housing and said insert and adapted to engage the dental implant, said retaining screw releasably adapted to secure said healing cap against the head of the dental implant.

2. The healing cap of claim 1 wherein said housing further comprises a top disposed at the patient's gingiva crest when installed in a patient's mouth, said top having an occlusal lip extending continuously about the periphery of said housing.

3. The healing cap of claim 2 wherein said housing has a lingual portion, said lingual portion being tapered downwardly.

4. The healing cap of claim 1 wherein said insert has a bottom surface defined by edges that are tapered to imitate the natural cavity of the tooth.

5. The healing cap of claim 1 wherein said housing further comprises an upper chamber having a bottom and said retaining screw further comprises a head, said head of said retaining screw being located within said upper chamber and said head being tightened against said bottom.

6. The healing cap of claim 5 wherein said upper chamber further comprises at least one inner surface, said at least one inner surface having at least one recess therein, said upper chamber having a light-cured material therein, said light-cured material extending into said at least one recess to lock said material in said upper chamber.

7. The healing cap of claim 1 wherein said coupling means comprises a connector for engaging the anti-rotational coupling on the head of the implant, said connector mating with the anti-rotational coupling.

8. The healing cap of claim 7 wherein said connector comprises an outer surface of a predetermined geometric shape.

9. The healing cap of claim 1 wherein said housing comprises a bottom chamber having at least one inner surface, said at least one inner surface having at least one recess therein, and wherein a retentive lip is received within said at least one recess.

10. The healing cap of claim 1 wherein said insert comprises a mesial side, a lingual side, a buccal side and a distal side, a top side and a bottom side, and a bore between said top side and said anti-rotational coupling, said bore being located a predetermined distance from said buccal and lingual sides.

11. The healing cap of claim 1 wherein said housing comprises a reusable material that is compatible with gingiva tissue.

12. The healing cap of claim 1 wherein said insert comprises a plastic material.

13. The healing cap of claim 1 wherein said housing further comprises an intermediate wall defining an upper chamber and a lower chamber, said intermediate wall having at least one hole therethrough for the passage of said retaining screw.

14. A system for creating a crown which replicates a tooth naturally residing at a predetermined position in the gingiva tissue of a patient, said crown being arranged for securement to a dental implant having a head including an antirotational coupling, said system comprising a healing cap, said healing cap forming a cavity in said gingiva tissue when installed in a patient's mouth whose shape replicates a portion of the tooth and comprising a housing and an insert, said housing having an outer surface including portions having at least two predetermined dimensions, said dimensions comprising the mesio-distal dimension of the neck of the tooth and the labio-lingual dimension of the neck of the tooth, said dimensions being representative of the anatomical dimensions of the corresponding portion of the tooth which was located within the gingiva tissue, said insert having coupling means to engage and mate with the anti-rotational coupling on the head of the dental implant, the anti-rotational coupling forming the opening to a threaded bore, said insert being releasably secured inside said housing by a securement means, said housing, said coupling means being adapted to be aligned with the anti-rotational coupling of the dental implant and further comprising a retaining screw passing through said housing, and said insert and the dental implant, said retaining screw adapted to releasably secure said healing cap against the head of the dental implant.

15. The system of claim 14 additionally comprising a plastic burn-out sleeve for surrounding a restorative castable cylinder used in forming a prepped tooth portion of said crown, said burnout sleeve comprising an outer surface and a tapered collar extending about the entire periphery of said outer surface, 16. The system of claim 15 wherein said outer surface of said burn-out sleeve corresponds to the dimensions of a naturally prepared tooth.

17. The system of claim 15 wherein said tapered collar comprises a side surface which forms a lower portion of said cavity and a top surface for support for said crown.

18. The system of claim 15 wherein said plastic burn-out sleeve further comprises a bore that conforms to the outer surface of a standard restorative castable cylinder.

19. The system of claim 15 additionally comprising a plastic hollow cylinder for disposition on top of said restorative castable cylinder.

20. The system of claim 19 wherein said plastic burn-out sleeve has a top with an opening therein and wherein, said cylinder has a top disposed coincident with said top opening of said plastic burnout sleeve.

21. The system of claim 14 additionally comprising a healing cap replica, said replica having the same dimensions as said housing of said healing cap.

22. The system of claim 14 additionally comprising an alignment indicator for verifying the orientation of the dental implant.

23. The system of claim 22 wherein said alignment indicator comprises a shaft having a proximal end and a distal end, said distal end having an anti-rotational coupling to matingly engage the anti-rotational coupling of the dental implant, said proximal end of said indicator having two members mutually perpendicular to said shaft and to each other.

\* \* \* \* \*